United States Patent [19]

Sandel et al.

[11] Patent Number: 4,605,124

[45] Date of Patent: Aug. 12, 1986

[54] DISPOSABLE COVER FOR SURGICAL LIGHT HANDLE

[75] Inventors: Dan Sandel; Michael Hoftman, both of Northridge, Calif.

[73] Assignee: Devon Industries, Inc., Los Angeles, Calif.

[21] Appl. No.: 521,626

[22] Filed: Aug. 9, 1983

[51] Int. Cl.[4] ............................................. B65D 69/00
[52] U.S. Cl. .................................... 206/223; 150/52 R
[58] Field of Search .............. 150/52 R; 206/223, 306

[56] References Cited

U.S. PATENT DOCUMENTS

| | | | |
|---|---|---|---|
| 2,714,912 | 8/1955 | Gonnella | 150/52 R |
| 3,110,336 | 11/1963 | Sukala, Jr. | 150/52 R |
| 3,228,445 | 1/1966 | Mayotte | 150/52 R |
| 3,473,682 | 10/1969 | Studen | 150/52 R |
| 3,632,014 | 1/1972 | Basile | 220/94 R |
| 3,648,887 | 3/1972 | Hartley | 220/94 R |
| 3,720,250 | 3/1973 | Goldberg et al. | 150/52 R |
| 3,738,173 | 6/1973 | Sato | 206/306 |
| 3,862,654 | 1/1975 | Goldberg et al. | 150/52 R |
| 3,929,018 | 12/1975 | Turner | 206/306 |
| 4,022,063 | 5/1977 | West et al. | 206/306 |
| 4,293,015 | 10/1981 | McGough | 150/52 R |

Primary Examiner—Joseph Man-Fu Moy
Attorney, Agent, or Firm—Poms, Smith, Lande & Rose

[57] ABSTRACT

A sterile cover for the handle on a surgical light is comprised of an integrally formed disposable plastic sheath generally in the shape of a unibody hollow cylinder with either a hollow inverse conical-shaped member or a dish shaped member at an open end of the cylinder. An alternative embodiment of the invention relates to an adapter kit having an adapter bushing, an adapter handle for threaded or snap-on attachment to the stud on any of a variety of lighting fixtures and sterile covers to allow the covers to be used on light fixtures having different sizes of handle mounting studs.

16 Claims, 13 Drawing Figures

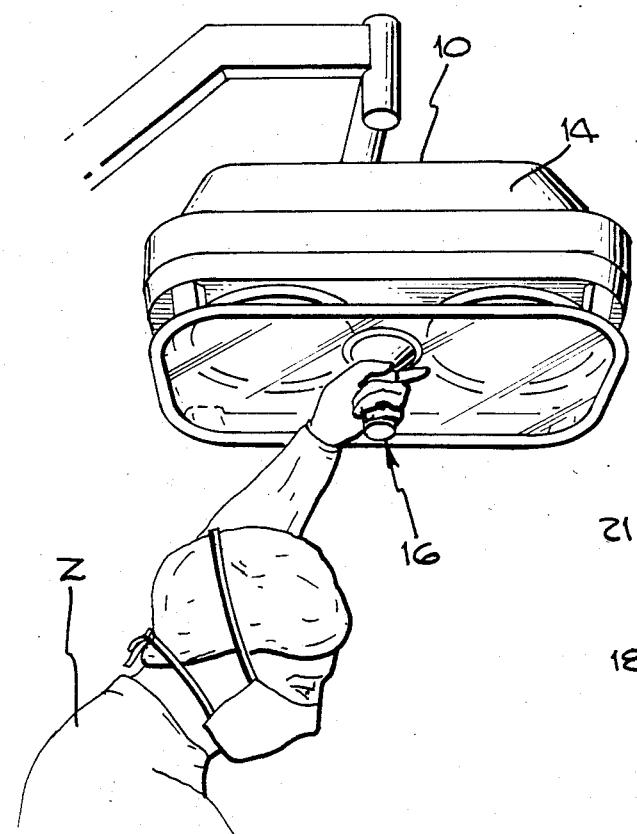
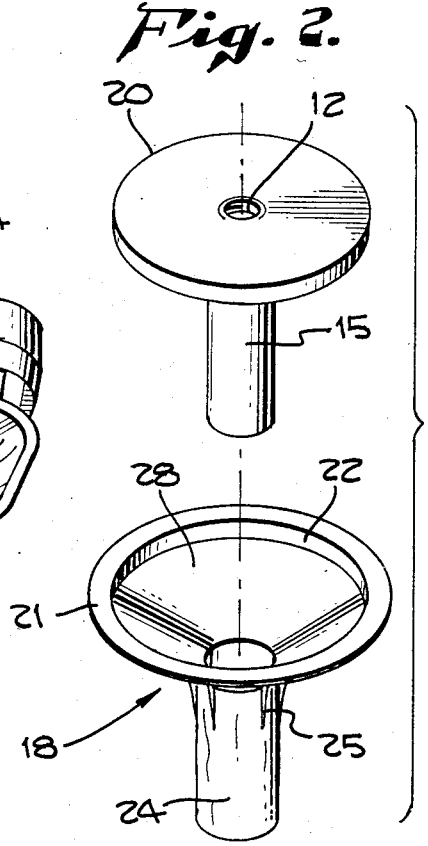
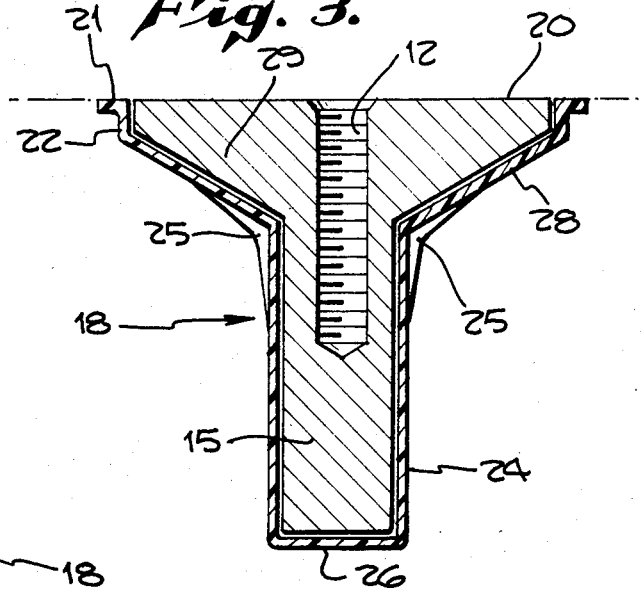
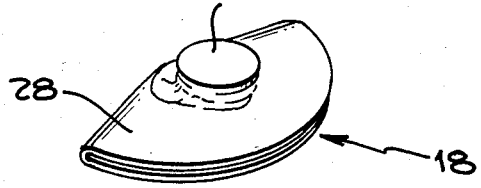

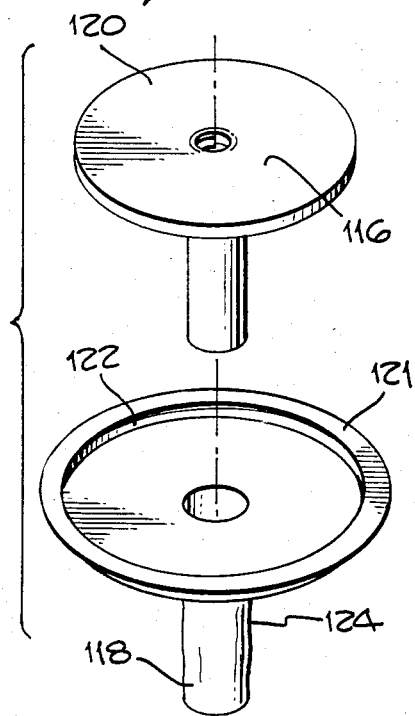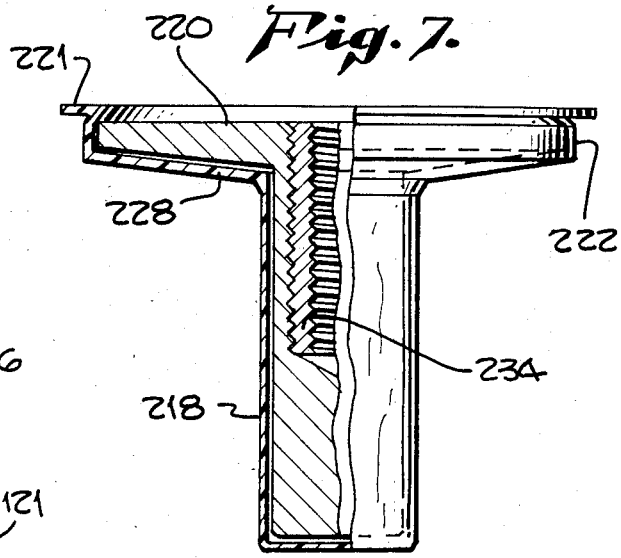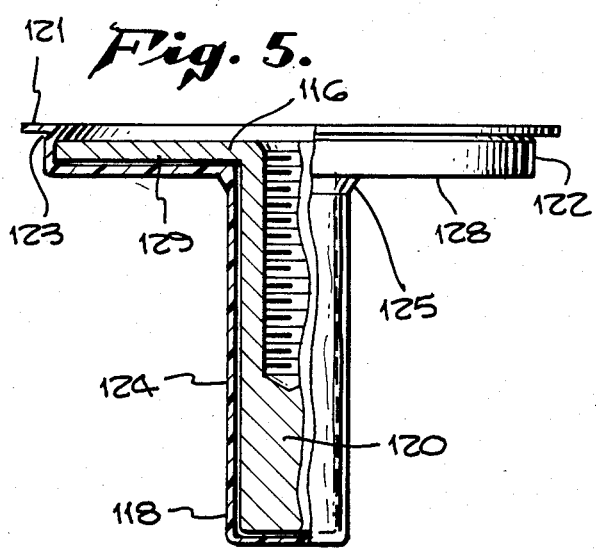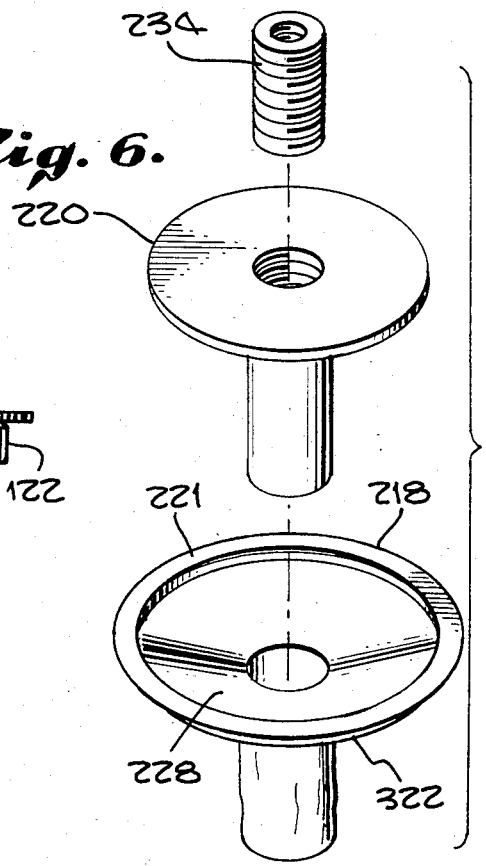

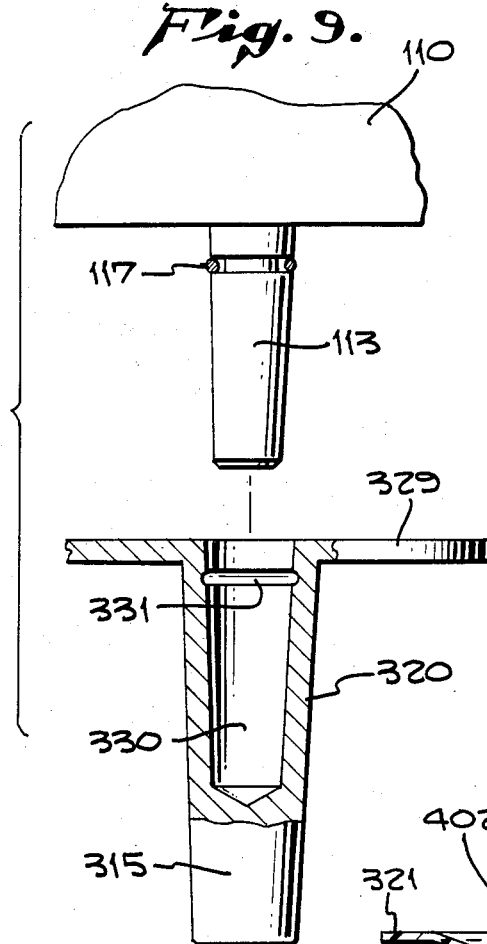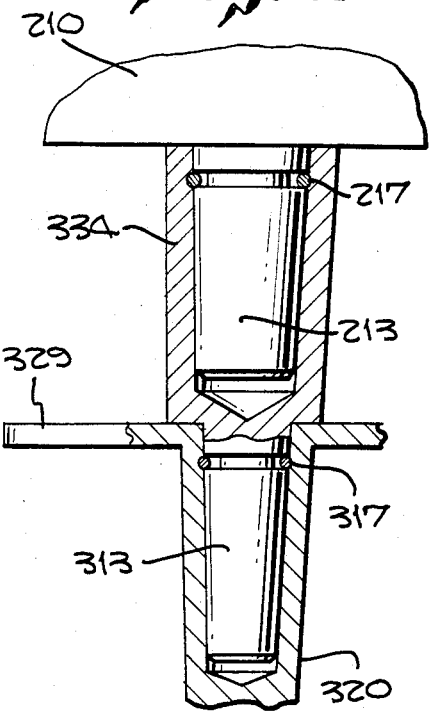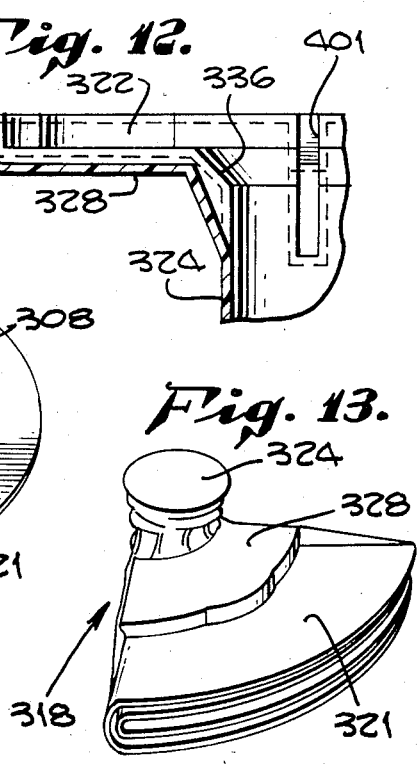

DISPOSABLE COVER FOR SURGICAL LIGHT HANDLE

BACKGROUND OF THE INVENTION:

The present invention relates in general to hospital surgery room equipment and specifically to a disposable cover for the handle of a surgical room light fixture which is normally positioned above the operating table and handled by the surgeon and or nurse during operations.

In operating rooms and surgical surroundings, special and unique lighting is employed due to the unique requirements for both high-powered lighting and the attainment of a sterile environment.

This lighting commonly consists of an arrangement of lights suspended from above the operating area so as to project and focus the rays upon the surgical area. Due to the use of such lighting, surgical personnel find it necessary to adjust the angle of incidence upon the operating areas or to bring the light closer to the area which is being operated on during surgery. To accomplish this task, the moveable lighting fixture usually has a handle situated in the middle of the light housing and depends therefrom.

To aid in the pursuit of cleanliness and in order to aid in the creation of a more sterile environment, the handle of the lighting housing must be sterile because of the constant contact with the hands of surgical personnel who are attempting to adjust the lighting. The handle must not become contaminated and render the environment not sterile.

OBJECTS OF THE INVENTION

Accordingly, it is an object of the present invention to provide a novel sterile cover for the handle on a surgical light fixture. It is a further object to provide such a surgical light fixture handle cover that is both inexpensive and easy to manufacture and which may be disposable. A further object of the present invention is to provide an adapter kit so that the handle cover of the present invention may be used with various type or size of light fixture handle.

SUMMARY OF THE INVENTION

Generally stated, the present invention comprises the provision of a disposable cover for the handle of the surgical room light fixture, which is normally positioned above the operating table and handled by the surgeon and or nurse during operations, the cover comprising a sterile, disposable thin walled impervious plastic or rubber like material body including a generally cylindrical or conical grip portion and a flange integral with said grip portion at an open end thereof, the opposite end of said grip being closed by an integral end wall whereby said cover body may be fit over said light fixture handle with said flange abutting portions of said fixture adjacent said handle.

More specifically, the flange may be of a generally flat or bell configuration and the grip may be collapsible thereon, the cylindrical or conical grip may be provided with a low coefficient of friction surface on its inside and a high coefficient of friction surface on its outside, the grip portion may be provided slightly undersized for the diameter of handle it is intended for whereby the grip portion has a elastically expanded snug fit about said handle when fitted thereon or may be of cone configuration for a snug fit to a conical shaped handle, and adhesive means may be preapplied to the underside of the flange whereby the flange may be pressed into an adhering fit against adjacent portions of the handle and/or fixture, the body flange and grip portions may be foldable and collapsible respectively to facilitate packaging the cover for storage prior to use on the handle, the flange preferably having integral folding creases therefor, the body flange may be provided with a peripheral rim having a laterally outwardly extending lip to overly adjacent portions of the fixture or handle, the upper circumference of the peripheral rim is preferably slightly undersize relative the handle flange to give a snap over fit relative thereto and reinforcing means including integral ribs may be provided integrally of the grip portion and flange for giving the flange and grip portion a reinforced predetermining configuration for facilitating the fit thereof to the handle.

Also contemplated within the present invention is a disposable surgical light fixture handle cover and adapter handle kit for use with surgical light fixtures having handle mounting threaded studs, or being of the snap-on type, of differing size, the kit comprising a surgical light fixture handle having a threaded or detented means bore of a given first size for mounting the handle to a mating threaded or detented means stud of a similar size, one or more disposable covers in accordance with the cover of the present invention and one or more adapter bushings having inner and outer threads or detent means to adapt said handle bore to fit preselected different sized light fixture studs.

BRIEF DESCRIPTION OF THE DRAWINGS

FIG. 1 is a perspective view showing a surgical lighting fixture and handle thereof equipped with an exemplary embodiment of the disposable cover of the present invention.

FIG. 2 is an exploded view of the disposable cover and handle of FIG. 1.

FIG. 3 is a cross-sectional view of the disposable cover and handle of FIG. 1.

FIG. 4 is an exploded view of a first alternative embodiment of cover designed to fit into a slightly modified version of surgical lamp handle.

FIG. 5 is a cross-sectional view of the cover and handle of FIG. 4 in assembled relation.

FIG. 6 is an exemplary embodiment of disposable cover and handle adapter kit of the present invention showing an adapter kit in exploded relation with a second alternative embodiment of cover therefor.

FIG. 7 is a cross-sectional view of the embodiment of kit of FIG. 6 when in assembled relation.

FIG. 8 is an exemplary view of the surgical light handle cover of FIG. 7 in accordance with the present invention in a folded and collapsed condition.

FIG. 9 is an exploded view of another exemplary embodiment of surgical light fixture stud of conical configuration with a first exemplary embodiment of detented, snap-on type conical handle therefor.

FIG. 10 is an assembled view of a second exemplary embodiment of surgical light fixture stud of conical configuration which is somewhat larger than that of FIG. 9 together with an adapter bushing for assembly of a second exemplary embodiment of detented, snap-on type conical handle therefor which is of a slightly smaller size then that illustrated in FIG. 9.

FIG. 11 is a third alternative embodiment of disposable cover, in accordance with the present invention, FIG. 12 is a detail cross-sectional view of a portion of the disposable cover of FIG. 11 taken therein along the plane XII—XII.

FIG. 13 is a perspective view of the disposable cover of FIGS. 11 and 12 shown in a folded and collapsed condition.

DETAILED DESCRIPTION OF THE PREFERRED EMBODIMENTS

Referring first to FIG. 1, a surgical lighting fixture 10 comprised of a body 14 and having a manual handle and cover assembly is shown at 16 which is meant to be used by a surgical attendant designated by the FIG. Z. The lighting structure is suspended over the head of the surgical attendant performing the surgical procedure. As can readily be seen in FIG. 1, the surgical attendant may make necessary adjustments to the lighting fixture orientation, including the angle of light incidence by use of the cover and handle assembly 16.

Referring now to FIGS. 2 and 3 the surgical lighting fixture handle member 20 having grip 15 is illustrated. The handle member of the surgical lighting fixture is attached to the underside of the lighting body 14, as shown in FIG. 1, by use of a threaded bolt designed to be received in the threaded bore 12.

In general, the first exemplary embodiment of cover member of the present invention, indicated generally at 18, includes a generally cylindrical grip portion 24, which has a closed and generally flat end wall 26, a flange 28, which is of hollow frustro-conical shape and has side walls to surround and fit the corresponding bell-shaped portion 29 of the handle; and an annular lip 21 extending laterally outwardly about the outer upstanding rim 22 of the conical flange 28. A plurality of reinforcing ribs or webs 25 may be formed in the cover extending vertically along portions of the cylindrical handle grip portion 24 and the conical shaped flange 28 to add rigidity to the cover as seen in FIG. 3 and to facilitate folding as seen in FIGS. 8 and 13. It is contemplated that an adhesive means can be applied to the interior portions of flange 28 and/or rim 22 and/or lip 21 in order to firmly attach the cover to the handle of the light fixture.

Referring to FIGS. 4 and 5, an alternative embodiment of the present invention of handle cover is shown. As can be seen from the illustrations of FIGS. 4 and 5, the handle member 120 of this embodiment is disc-shaped with a flat underside surface 129 as seen in FIG. 5. The exemplary cover 118 has a corresponding flat configuration flange 128, a cylindrical portion 124 and a reinforcing fillet 125. As can be seen in FIG. 5, and as is particularly contemplated within the present invention, the peripheral rim 122 extends substantially vertically about the outer periphery of the generally flat flange portion 128 of the exemplary cover and next in at a reduced diameter portion along its upper periphery 123 to snap fit over and about the generally flat flange 116 of the exemplary handle 120 as seen in FIG. 5. This exemplary cover also has a surrounding, laterally outwardly extending lip 121 which is held up against the surrounding portions of the light fixture by the snap fit retention of the cover to the fixture handle 120 by virtue of the snap fit of rim 122 about handle flange 116.

Referring now to FIGS. 6 and 7, another exemplary embodiment of the present invention illustrating an adapter kit for adapting the handle cover for use in any light fixture is illustrated. The exemplary kit comprises essentially three types of parts: one or more internally and externally threaded bushings 234, an internally threaded adapter handle 220, and one or more of a second alternative embodiment of the disposable handle cover of the present invention illustrated at 218. The adapter bushing 234 is thread on its inside to attach to a mating threaded on a threaded bolt or stud extending from the light fixture body 14. The bushing 234 also has outside threads which are used to attach the bushing to the adapter handle 220. The light fixture handle flange may be either of the disc-shaped variety, the conical-shaped variety or other shape. Accordingly, the corresponding shape of the exemplary cover is of a mating configuration and includes a mating flange 228, snap fit rim 222 and surrounding lip 221 as seen in FIG. 7.

As would be discussed more fully hereinafter with regard to the embodiment of FIGS. 11 through 13, the disposable cover in accordance with the present invention is particularly adapted to be folded into a fairly small configuration for ease of storage prior to use, as well as for disposal after use. As seen in FIG. 8, the exemplary embodiment of disposal cover of FIGS. 2 and 3 is illustrated with the cover grip portion 24 vertically collapsed by virtue of its thin wall, flexible material construction. The cover flange 28 may be folded over once, as illustrated, or also a second time to give the flange a triangular or pie shape for packaging and/or storage as will be discussed subsequently with the embodiment of cover illustrated in FIG. 13. The cover may be composed of any elastic sterilizable material such as plastic, synthetic rubber, silicone, or laytex or any other material that will remain impervious even while exposed to sterization by heating. The material should be preferably thin and pliant and have a low coefficient of friction surface on the inside and a high coefficient of friction surface on the outside in order to both allow easy assembly onto the handle while allowing the surgical attendant to easily grip and interact with the handle cover exterior. Preferably the cylindrical grip portion is formed slightly undersized for a cylindrical handle, or of conical shape for a conical handle so that it is slightly expanded, elastically in a snug fit, upon assembly to the handle.

Referring now to FIG. 9, an alternative embodiment of light fixture 110 is illustrated having a conical configured mounting stud 113 having a detent means, in the exemplary embodiment of snap ring 117 for receiving handle 320 which has a conical configured grip 315, a generally flat flange 329 and a hollow bore 330 having a mating detent means, being a groove 331 in the exemplary embodiment, for receiving in snap fit fashion the snap ring 117 on assembly of handle 320 to the stud 113.

As is contemplated within the present invention, an adapter kit in accordance with the present invention may include an adapter member 334 for mounting to a slightly larger stud 213 of a further exemplary embodiment of light fixture 210 as seen in FIG. 10. A snap ring 217 is provided for mounting into a mating groove of adapter member 334 so that it can be mounted to stud 213 in a snap fit. Auxiliary stud 313 is formed integrally of the adapter member 334 with a detent means comprising a snap ring 317 to facilitate receiving the handle 320 of FIG. 9 to thereby mount it to the larger sized stud 213 of the alternative fixture 210. From the foregoing, those skilled in the art can appreciate that the handle for the disposable cover adapter kit in accordance with the present invention can be made of a standard size and adapted by appropriate threaded or snap-on, or other alternative embodiments of, adapter members to fit varying light fixture stud constructions.

Referring now to FIGS. 11 through 13, a thrid exemplary embodiment of disposable light fixture handle cover, in accordance with the present invention, is illustrated generally at 318. As perhaps is best seen in FIG. 11, the exemplary disposable cover indicated generally at 318 includes a generally cylindrical rip portion 324, which could be of conical configuration, which merges through beveled portion 336 into a generally flat flange portion 328 which is provided with a vertical rim 322 and a surrounding, fairly broad and flat lip 321. As is particularly contemplated within the present invention, and illustrated by the present embodiment of disposable cover, folding creases may be provided in the cover as shown by the exemplary folding creases 400, 401, 402 and 403. As seen in perspective view in FIG. 11, and in cross section in FIG. 12, the folding creases of the exemplary embodiment, as crease 402, extend through portions of the lip 321 rim 322 and flange 328, as well as the beveled portion 336 to provide folding lines through the otherwise fairly stiff cover construction for these parts in the embodiment of FIGS. 11 and 12. The creases may also be provided only in the flange 328 where it is desired to maintain lip and rim rigidity, as when the snap fit function of the rim is desired as seen in FIGS. 5 and 7. The provision of such folding creases 400-404, in accordance with the present invention, greatly facilitate the folding of the disposable cover once along a first opposed pair of creases and then secondly along a second pair of opposed creases to provide the pie shaped folded configuration of cover, indicated generally at 318, in FIG. 13. The thin walled grip portion 324 may be collapsed vertically as illustrated to facilitate the packaging, storage and disposal of the exemplary disposable cover.

From the foregoing description it should be apparent to those skilled in the art that numerous modifications and alternations are possible without departing from the spirit and scope of the present invention. Accordingly, the scope of the present invention is to be limited only the scope of the appended claims.

What is claimed is:

1. A disposable cover for the handle of a surgical room light fixture which is normally positioned above the operating table and handled by the surgeon during operations, said handle having a generally cylindrical grip depending form a bell-shaped portion adjacent the light fixture, said cover comprising:

a sterile, disposable thin walled impervious plastics or rubber like material body including a generally cylindrical and hollow grip portion and a flange, integral with said grip portion at an open end thereof, the opposite end of said grip being closed by an integral end wall, and wherein said flange is of a generally bell like configuration for mating engagement with said handle bell-shaped portion wherein said cover body may be fitted over said light fixture handle grip portion with said flange abutting and covering said bell-shaped portion of said handle adjacent said fixture, wherein an adhesive material is preapplied to the interior portions of said flange whereby said flange may be pressed into an adhering fit against adjacent portions of said handle and/or fixture.

2. A disposable cover for the handle of a surgical room light fixture which is normally positioned above the operating table and handled by the surgeon during operations, said handle having a generally cylindrical grip depending from a bell-shaped portion adjacent the light fixture, said cover comprising:

a sterile, disposable thin walled impervious plastics or rubber like material body including a generally cylindrical and hollow grip portion and a flange integral with said grip portion at an open end thereof, the opposite end of said grip being closed by an integral end wall, and wherein said flange is of a generally bell-like configuration for mating engagement with said handle bell-shaped portion wherein said cover body may be fitted over said light fixture handle grip portion with said flange abutting and covering said bell-shaped portion of said handle adjacent said fixture, and reinforcing means including integral ribs are provided integrally of said grip portion and flange for giving said flange and grip portion a reinforced predetermined configuration for facilitating the fit thereof to said handle.

3. A disposable cover for the handle of a surgical room light fixture which is normally positioned above the operating table and handled by the surgeon during operations, said handle including a handle grip depending from a handle flange adjacent said fixture, said cover comprising:

a sterile, disposable thin walled imperivous plastics or rubber like material body including a generally hollow grip portion and a flange integral with said grip portion at an open end thereof, whereby said cover body may be fitted over said light fixture handle, and wherein reinforcing means including a plurality of spaced ribs are provided integrally of said grip portion and flange for giving said flange and grip portion a reinforced and predetermined configuration for facilitating the fit thereof to said handle.

4. The disposable cover of claim 3 wherein said cylindrical grip is provided with a low coefficient of friction surface on its inside and a high coefficient of friction surface on its outside.

5. The disposable cover of claim 3 wherein said grip portion is provided slightly undersized for the diameter of the handle it is intended for whereby said grip portion has an elastically expanded snug fit about said handle when fitted thereon.

6. The disposable cover of claim 3 wherein said body flange and grip portions are foldable and collapsible respectively to facilitate packaging said cover for storage prior to use on said handle.

7. The disposable cover of claim 3 wherein said body flange is provided with folding creases to facilitate the folding thereof.

8. The disposable cover of claim 3 wherein said body flange is provided with an outer upstanding rim covering side portions of said handle flange adjacent said fixture and mounting an integral peripheral lip extending laterally outwardly outer the other rim away from said handle flange to overlie adjacent portions of the fixture.

9. The disposable cover of claim 3 wherein said body flange is provided with a generally upstanding circumferential rim about the periphery thereof and said rim has an upper reduced inner diameter portion thereof providing a smaller diameter for said rim about the upper periphery thereof to facilitate a snap fit of said body flange rim about a flange of the handle of the surgical room light fixture.

10. An assembly of disposable cover, replacement light fixture handle and handle mounting adapter for replacing a conventional light fixture handle of a surgery room light fixture and providing for disposable sterile covering of the replacement handle, said assembly comprising:
 a replacement light fixture handle having a grip portion depending from a handle flange and means for receiving an adapter mounting member for mounting of said replacement handle to said fixture;
 an adapter mounting member including first interconnecting means for interconnecting said member to said replacement handle and second interconnecting means for interconnecting said member to said light fixture on removal of the fixture conventional handle; and
 a sterile, disposable thin walled imperivous plastics or rubber like material cover body including a generally cylindrical and hollow grip portion and a flange integral with said grip portion at an open end thereof, said flange being of a generally like configuration to that of said handle flange for mating engagement with said handle flange, whereby said cover body may be fitted over and closely fitted to said replacement light fixture handle.

11. The assembly of claim 10 wherein said cylindrical grip is provided with a low coefficient of friction surface on its inside and a high coefficient of friction surface on its outside.

12. The assembly of claim 10 wherein said grip portion is provided slightly undersized for the diameter of the handle it is intended for whereby said grip portion has an elastically expanded snug fit about said handle when fitted.

13. The assembly of claim 10 wherein said body flange and grip portions are foldable and collapsible respectively to facilitate packaging said cover for storage prior to use on said handle.

14. The assembly of claim 10 wherein said body flange is provided with folding creases to facilitate the folding thereof.

15. The assembly of claim 10 wherein said body flange is provided with an outer upstanding rim covering side portions of said handle flange adjacent said fixture and mounting an integral peripheral lip extending laterally outwardly about the outer rim away from said handle flange to overlie adjacent portions of the fixture.

16. The assembly of claim 10 wherein said body flange is provided with a generally upstanding circumferential rim about the periphery thereof and said rim has an upper inner diameter portion thereof providing a smaller diameter for said rim about the upper periphery thereof to facilitate a snap fit of said body flange rim about a flange of the handly of the surgical room light fixture.

* * * * *